(12) United States Patent
Khan et al.

(10) Patent No.: US 8,771,243 B2
(45) Date of Patent: Jul. 8, 2014

(54) WOUND TREATMENT SYSTEM

(75) Inventors: Joseph Khan, Kalamazoo, MI (US);
Jonathan Schoeff, Ft. Wright, KY (US)

(73) Assignee: University of Cincinnati, Cincinnati, OH (US)

( * ) Notice: Subject to any disclaimer, the term of this patent is extended or adjusted under 35 U.S.C. 154(b) by 1417 days.

(21) Appl. No.: 12/023,251

(22) Filed: Jan. 31, 2008

(65) Prior Publication Data

US 2008/0287892 A1 Nov. 20, 2008

Related U.S. Application Data

(60) Provisional application No. 60/887,715, filed on Feb. 1, 2007.

(51) Int. Cl.
*A61F 13/00* (2006.01)
*A61M 1/00* (2006.01)
*A61M 27/00* (2006.01)

(52) U.S. Cl.
USPC ............................ 604/313; 604/290; 604/541

(58) Field of Classification Search
USPC ........... 604/313, 19, 289, 290, 317, 319, 541; 602/42
See application file for complete search history.

(56) References Cited

U.S. PATENT DOCUMENTS

| 4,112,947 A * | 9/1978 | Nehring ........................... 604/30 |
| 5,549,587 A | 8/1996 | Norton |
| 5,636,643 A * | 6/1997 | Argenta et al. ............... 128/897 |
| 5,938,647 A | 8/1999 | Smith |
| 5,989,235 A | 11/1999 | Quacquarella et al. |
| 6,071,267 A | 6/2000 | Zamierowski |
| 6,264,979 B1 * | 7/2001 | Svedman ...................... 424/449 |
| 6,328,719 B1 | 12/2001 | Holtermann et al. |
| 7,338,482 B2 * | 3/2008 | Lockwood et al. ........... 604/543 |

OTHER PUBLICATIONS

Hollington, P. et al., An 11-year experience of enterocutaneous fistula, British Journal of Surgery, 2004; 91:1646-1651, John Wiley & Sons Ltd.

Cro, C. et al., Vacuum assisted closure system in the management of enterocutaneous fistulae, Postgrad. Med. J., 2002; 78:364-365.

Erdmann, D., M.D. et al., Abdominal Wall Defect and Enterocutaneous Fistula Treatment with the Vacuum-Assisted Closure (V.A.C.) System, Lippincott Williams & Wilkins, Inc., Dec. 2001; 108(7):2066-2068.

* cited by examiner

*Primary Examiner* — Tatyana Zalukaeva
*Assistant Examiner* — Benedict L Hanrahan
(74) *Attorney, Agent, or Firm* — Wood, Herron & Evans, L.L.P.

(57) ABSTRACT

A wound treatment system includes a sponge including a first surface adapted to confront a wound bed of a patient, a drape in contact with a second surface of the sponge, and a vacuum source for distributing a vacuum force through the sponge. The system also includes a wound separator having a sidewall defining an interior chamber, wherein at least a portion of an exterior of the sidewall confronts at least an interior portion of the sponge. An ostomy appliance is operatively connected to the wound separator to receive substances passing out of the wound separator.

11 Claims, 2 Drawing Sheets

WOUND TREATMENT SYSTEM

FIELD OF THE INVENTION

The present invention generally relates to the management and treatment of wounds, and particularly relates to management and treatment of fistulas in complex wounds.

BACKGROUND

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Wound management significantly affects many aspects of health care and is involved in many medical procedures. For example, wound care typically involves absorbing and/or draining blood, serum, and other body fluids from the patient. In particular, various surgical procedures also require fluid drainage. For example, post operative fistulas [e.g., enterocutaneous ("EC") fistulas] can develop, which have fluid drainage that needs to be managed. Such fistulas may develop in the setting of malnutrition, cancer, inflammatory disease, etc. They are commonly associated with abdominal operations in the setting of inflammatory bowel disease (e.g., Crohn's disease).

Figure 1:
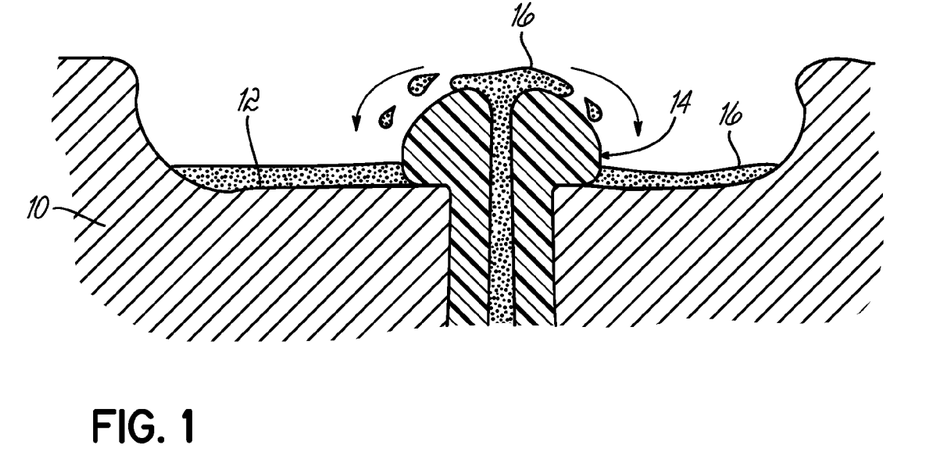
FIG. 1 is a cross-sectional view of the environment for a wound treatment system in accordance with the principles of the present invention.

A fistula is an abnormal connection or passageway between organs or vessels that normally do not connect. For example, the EC fistula arises between the intestine (namely from the duodenum, the jejunum or the ileum) and the skin surface. As a result, stool or other enteric substances will pass through the fistula (i.e., from the intestine to the skin surface) and pool up in a wound bed (such as may be present following surgery), thereby preventing wound healing. For example, as shown in FIG. 1, a patient body 10 includes a wound bed 12. A fistula 14 is shown as being in fluid communication with the wound bed 10 such that stool 16 may pass through the fistula 14 and pool in the wound bed 12, thereby retarding wound healing by breaking down skin, soft tissue, and/or fascia.

EC fistulas can have severe consequences. Mortality rates have been reported as high as 20%-65%. Further, health care costs are high, related in large part to time-intensive inpatient management of complex abdominal wounds. Current procedures for wound treatment often require the patient to remain at a hospital, clinic, etc., because the wound requires near-constant regimented attention to ensure healing. And thus, wound care remains a predominant source of morbidity and health care costs. Current approaches to wound management focus on diversion of enteric substances to avoid breakdown of associated skin, soft tissue, and/or fascia.

For example, various types of porous, absorbent dressing materials have been used for dressing wounds to accumulate body fluids. The dressing materials facilitate drainage and also collection and disposal of the fluids. A disadvantage with many conventional dressings is that they require changing to reduce risks of infection and to maintain effectiveness. However, dressing changes can add significantly to treatment costs and are associated with patient discomfort and medical risks such as infection and damage to reepithelialized tissue. Accordingly, vacuum sources have been employed to drain wounds. For example, U.S. Pat. No. 6,071,267 pertains to wound dressings, fluid connections, and fastening systems in connection with vacuum-assisted wound drainage. Such devices are often referred to as vacuum-assisted closure, or "VAC®" devices.

Figure 2:
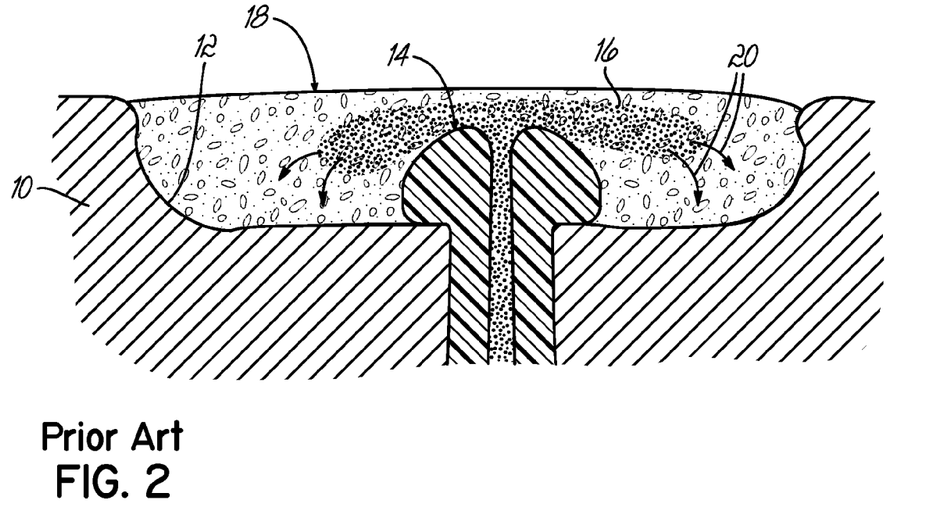
FIG. 2 is a prior art view of a system for treating a wound including a fistula.

VAC® devices have been somewhat successful in promoting wound healing. VAC® technology consists of an airtight dressing that provides drainage to the wound bed under a vacuum. The effectiveness of VAC® technology with fistulas, however, has been limited, as it is unable to efficiently accommodate fistula output. In particular, and referring to FIG. 2, the VAC® dressing uses a sponge 18 kept in a low pressure environment to promote wound healing. (Other components of the VAC® device are not shown in FIG. 2.) However, the sponge 18 clogs quickly with the thick stool 16 from the fistula 14 and results in pooling of stool, and thus further wound breakdown. Further, once clogged, the sponge 18 acts as a wick, allowing equal distribution of stool across the entire wound bed (as at 20), thereby further stunting wound repair.

Thus, an effective wound treatment system is needed. Further, a system that reduces the time and costs of current systems is desirable.

SUMMARY

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

One aspect of the present invention provides a wound separator including at least one sidewall having first and second ends and defining an interior chamber. At least the first end is open, and the at least one sidewall is adapted to be placed in surrounding relationship relative to an opening in a wound bed, such as in surrounding relationship to a fistula. Thus, the wound separator physically separates the fistula from the remainder of the wound bed, such that any stool, or other enteric substances, that pass through the fistula are prevented from communicating with the wound bed outside of the wound separator. As a result, wound healing is promoted in that enteric substances are diverted from the wound bed, thereby reducing the breakdown of soft tissue, skin, etc., and lowering the incidence of infection.

The wound separator may be used with other components to promote wound healing and/or to reduce the time-intensity and/or cost of wound healing. Thus, another aspect of the present invention provides a wound treatment system including the wound separator as described above, and an ostomy appliance (e.g., an ostomy bag) operatively coupled to the wound separator. As above, at least the first end of the wound separator is open, and the at least one sidewall is adapted to be placed in surrounding relationship relative to a fistula. The second end of the wound separator is also open and is in fluid communication with an interior chamber of the ostomy appliance. As a result, any stool passing from the fistula will pass through the interior chamber of the wound separator and ultimately into the interior chamber of the ostomy appliance.

Yet another aspect of the present invention provides a wound treatment system including the wound separator, as described above, and a device including absorbent dressing materials and/or a vacuum source (e.g., a VAC® device). Thus, this aspect of the present invention includes a sponge having a patient-confronting surface, which is positioned facing the wound bed. The sponge may be an open-cell or closed-cell structure, (an open-cell structure includes a plurality of passages communicating with the surface of the wound bed).

A drape is placed over the sponge in contact with an outer surface thereof. A vacuum tube with opposite ends is connected to the sponge and a vacuum source. These are used to distribute a vacuum through or around the sponge. The wound separator, as described above, is positioned in surrounding relationship to a fistula, with at least a portion of an exterior of the wound separator confronting the sponge.

This aspect of the present invention thus combines the use of a device, such as a VAC® device, in wound healing and the concept of diverting stool or other enteric substances away from a wound bed. The VAC® device thus promotes healing of the wound while stool is diverted from the wound bed into a traditional ostomy bag, rather than pooling up and wicking via the VAC® sponge across the wound bed. In this way, the wound bed remains clean. More particularly, stool is prevented from entering the wound bed by using the size-matched wound separator and a leak-resistant wound sealant, thereby allowing the VAC® sponge to promote wound healing. The wound sealant aids in retaining the wound separator in place over the fistula.

Thus, the device of the present invention incorporates the VAC® dressing's proven healing properties while stabilizing the wound and allowing the patient to undergo dressing changes every three days, for example, instead of twice daily, which is the time period for wound dressing changes previously employed with the sole use of the VAC® device in wounds that produce significant drainage from fistulous output. Thus, patient compliance with the wound healing regimen is improved, and the device of the present invention enables patients to be discharged to home rather than remaining in a hospital, thereby decreasing healthcare costs.

Various features discussed below in relation to one or more of the exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention will become better understood when the following detailed description is read with reference to the accompanying figures in which like characters represent like parts throughout the figures, wherein.

DETAILED DESCRIPTION OF EXEMPLARY EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 3:
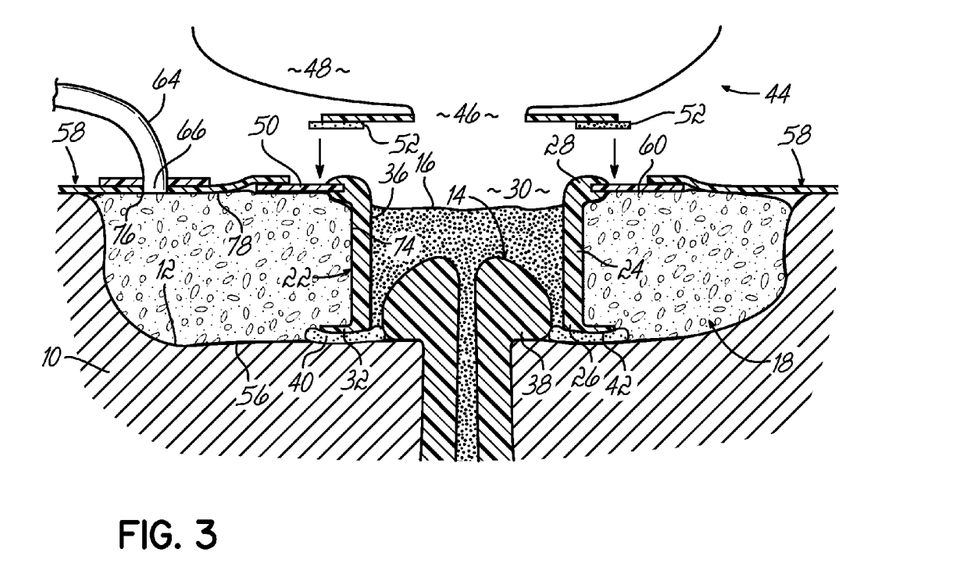
FIG. 3 is a cross-sectional view of a wound treatment system in accordance with the principles of the present invention associated with a fistula of a wound site.
Figure 4:
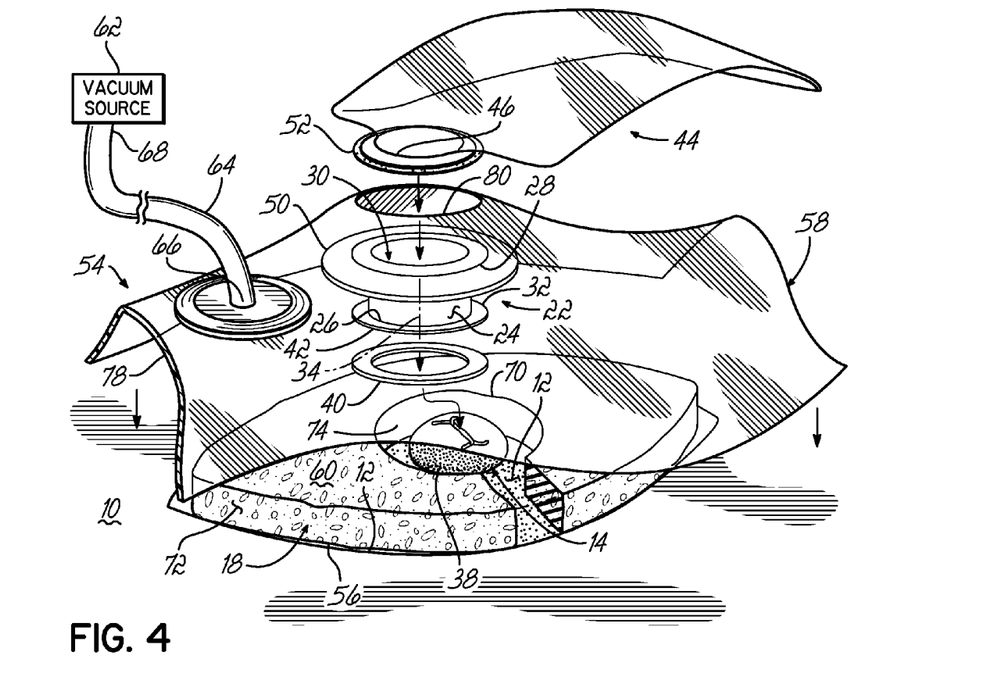
FIG. 4 is an exploded view of the wound treatment system in accordance with the principles of the present invention.

Referring now to FIGS. 3-4, one aspect of the present invention provides a wound separator 22 including at least one sidewall 24 having first and second ends 26, 28 and defining an interior chamber 30, wherein the sidewall 24 is adapted to be placed in surrounding relationship relative to a wound site, and particularly, in one embodiment, to surround a fistula 14. At least the first end 26 of the wound separator 22 is open. This first end 26 is adapted to be placed in confronting relationship with a patient surface, which may be a skin surface or a wound bed 12, for example.

Thus, the wound separator 22 is used to physically separate the fistula 14 from the remainder of the wound bed 12, such that any stool 16, or other enteric substances, that pass through the fistula 14 are prevented from communicating with the wound bed 12. As used herein, the "wound bed" is any area of the patient body 10 that has sustained trauma. And the "fistula" is the abnormal connection between an organ or vessel internal to the patient body 10 and a surface of the wound bed 12. Thus, the fistula 14 presents on at least a portion of the wound bed 12. Further, as will be recognized by those skilled in the art, while the at least one sidewall is depicted as cylindrical with a circular cross-section in the illustrated embodiment, such a shape is merely exemplary and further shapes of at least one sidewall (e.g., cross-sections that are ovoid, etc.) may be used (i.e., as a continuous sidewall). Alternatively, more than one sidewall may be used to provide a wound separator having cross-sections of other shapes (e.g., square, rectangle, rhomboid, etc.). Such sidewalls may be integral with one another, or may be separate and operatively connected to one another.

In the illustrated embodiment, the wound separator 22 is placed in a wound bed 12 such that the sidewall 24 surrounds a fistula 14 or other wound opening. By being so positioned, the wound separator 22 separates the fistula 14 from the remainder of the wound bed 12. This separation prevents any stool 16 or other enteric substance passing out of the fistula 14 from coming into contact with the wound bed 12 surrounding the fistula 14 (outside the wound separator 22) as the stool 16 will be at least initially retained within the interior chamber 30 of the wound separator 22. This promotes healing of the wound bed 12 by preventing breakdown of the wound bed 12 and lowering the chances for infection. Additionally, prior to placing the wound separator 22 in proximity to a fistula 14, the wound bed 12 and surrounding area may be cleaned. Further, a therapeutic treatment, such as a skin graft or pharmaceutical preparation (not shown), may be applied to the wound bed 12. As will be recognized by those skilled in the art, while the description here only discusses a single wound separator 22, more than one fistula 14 may present in a wound bed 12, and thus multiple wound separators 22 can be used to surround multiple fistulas 14.

The wound separator 22 may be made of any material suitable for the purposes described above, as will be recognized by those skilled in the art. Thus, in certain embodiments, the wound separator 22, or at least a portion thereof, may be made of any biocompatible materials, for example, plastics. In one particular embodiment, the sidewall 24 may be a latex rubber. Alternatively, other materials may be used, for example, an elastomeric acrylonitrile butadiene styrene ("ABS") or urethane. Further, as will be recognized by those skilled in the art, the wound separator 22 can be sized and shaped to accommodate all different sizes and shapes of fistulas 14.

In certain embodiments, such as the illustrated embodiment, the first end 26 of the sidewall 24 of the wound separator 22 may include a first flange 32 extending outwardly therefrom (outwardly relative to a longitudinal axis 34 of the wound separator 22). The first flange 32 of the wound separator 22 is adapted to confront the wound bed 12 of a patient body 10. Thus, in use, the wound separator 22 is positioned on a patient body 10 such that the inner surface 36 of the sidewall 24 surrounds a fistula 14 with the first flange 32 located in proximity to the base 38 of the fistula 14, and to the wound bed 12. As shown in the illustrated embodiment, the first flange 32 is integral with the sidewall 24. However, this is merely exemplary, as the first flange 32 and sidewall 24 may be separate components that are operatively connected to one another.

Further, a sealant 40 may be associated with the first flange 32. In particular, the sealant 40 may contact at least a portion of a lower surface 42 of the first flange 32 of the wound separator 22. In order to separate the fistula 14, and any stool 16 associated therewith, from the wound bed 12 of the patient body 10, the sealant 40, which may be a viscous sealing agent that is not readily dissolved by the output from the fistula 14, is applied to the wound bed 12 around the base 38 of the fistula 14. Alternatively, the sealant 40 may be incorporated into the wound separator 22 prior to the wound separator 22 being placed in proximity to the wound bed 12.

In either embodiment, the sealant 40 is ultimately positioned so as to contact and confront at least a portion of the lower surface 42 of the first flange 32. Thus, when the wound separator 22 is positioned in proximity to a wound bed 12 and surrounding a fistula 14, at least some sealant 40 is positioned between the first flange 32 and the wound bed 12. The sealant 40, in this position, serves at least two functions. First, it has adhesive qualities that adhere to the wound separator 22 and the wound bed 12, to hold the wound separator 22 in place surrounding the fistula 14. This ensures that the wound separator 22 will remain in its proper place during the wound treatment process and will not shift or otherwise move away from the fistula 14 due to movement of the patient body 10, for example. Second, the sealant 40 forms a seal between the wound separator 22 and the wound bed 12, such that any stool 16 or other enteric substance that exits the fistula 14 cannot access the wound bed 12 outside of the wound separator 22 via any path between the first flange 32 and the wound bed 12, since no such path exits due to the sealant 40. In order to serve the above functions, the sealant, in certain embodiments, may be a tacky substance or a substance that can become tacky under certain conditions. Thus, the sealant has adhesive qualities. In particular, in certain embodiments, the sealant may be any biocompatible substance that is sufficient for the above-described functions. And in one particular embodiment, the sealant is an ostomy paste. Such an ostomy paste is commercially available from Coloplast Corporation of Marietta, Ga. (a subsidiary of Coloplast Group of Humlebaek, Denmark).

Thus, in use, the first end 26 of the wound separator 22 is placed in a confronting relationship with the wound bed 12 of a patient body 10. The second end 28 of the wound separator 22 may also be open. Thus, any stool 16 that progresses out of the fistula 14 and into the interior chamber 30 defined by the sidewall 24 of the wound separator 22, may eventually exit the open second end 28 of the wound separator 22. Once the stool 16 so exits, it can move into a second component of the wound treatment system, the second component being associated with the wound separator 22. For example, the second component may be an ostomy appliance 44. And thus, another aspect of the present invention provides a wound treatment system including a wound separator 22 including at least one sidewall 24 having first and second ends 26, 28, and an ostomy appliance 44 operatively coupled to the second end 28 of the wound separator 22. In such an embodiment, an opening 46 in the ostomy appliance 44 can be placed in register with the second end 28 of the wound separator 22 such that any stool 16 exiting the second end 28 of the interior chamber 30 of the wound separator 22 ultimately enters an interior chamber 48 of the ostomy appliance 44.

In alternate embodiments, the second end 28 of the wound separator 22 may be closed. Such a wound separator 22 with a closed second end 28 may be used with fistulas 14 of small size and small wound beds 12, which will heal more rapidly. Alternatively, the second end 28 may be closed by another component, such as a drape of a VAC® device.

Regardless of the nature or type of the second component, the wound separator 22 may further include a second flange 50 operatively coupled to and extending radially outwardly from the second end 28. This second flange 50 may be used to facilitate attachment to the second component of the wound treatment system of the present invention. In particular embodiments, the second flange 50 comprises Opsite® (clear ABS). As shown in the illustrated embodiment, the second flange 58 and sidewall 24 are separate components that are operatively connected to one another. However, this is merely exemplary, as the second flange 50 and sidewall 24 may be integral in alternate embodiments.

Further, a sealant 52 may be associated with the second flange 50 of the wound separator 22. In particular, the sealant 52 may contact and confront at least a portion of an upper surface of the second flange 50 of the wound separator 22. The second flange 50 is adapted to confront the second component of the wound treatment system. In one embodiment, this second component may be an ostomy appliance 44 as described above. In such an embodiment, the sealant 52 is positioned such that when the ostomy appliance 44 is associated with the wound separator 22, the sealant 52 is positioned between the second flange 50 and the ostomy appliance 44. Particularly, the sealant 52 may contact a circumference around an opening 46 of the ostomy appliance 44 that is in register with the second end 28 of the wound separator 22. The sealant 52, in this position, serves at least two functions. First, it may have adhesive qualities to adhere to the wound separator 22 and to the ostomy appliance 44 such that the two are operatively coupled. This ensures that the wound separator 22 will remain in its proper place relative to the ostomy appliance 44. Second, the sealant 52 forms a seal between the wound separator 22 and the ostomy appliance 44, such that any stool 16 or other enteric substance that exits the fistula 14 cannot access the wound bed 12 outside of the separator by progressing between the second flange 50 and the ostomy appliance 44, since no such path exits due to the sealant 52. Rather, the stool 16 will progress into the interior chamber 48 of the ostomy appliance 44 once it exits the passageway of the wound separator 22 through the second end 28 of the wound separator 22. Thus, the sealant, in certain embodiments, may be a tacky substance or a substance that can become tacky under certain conditions. In particular, in certain embodiments, the sealant may be any substance that is sufficient for the above-described functions. And in one particular embodiment, the sealant is a pressure-sensitive adhesive tape or spray. In one particular embodiment, the sealant is 7730 Medical Adhesive Spray, which is commercially available from Hollister, Inc. of Libertyville, Ill.

While there are differing types of ostomy appliances, in the illustrated embodiment, the ostomy appliance 44 is an ostomy bag 44. An ostomy bag 44, as is well known to those skilled in the art, is a pouch that is employed to collect waste material (e.g., stool 16 or other enteric substances) that exits a patient's body. This stool 16 may exit through a stoma (i.e., through an artificial, permanent opening, surgically created in the patient's skin and connected to the intestine or to the bladder). As used herein, the ostomy bag 44 is used to ultimately collect waste materials that exit a patient's body through a fistula 14.

Ostomy bags typically include a pouch of plastic material that is moisture-impermeable and has an odor-barrier. The ostomy bag 44 includes an opening 46 to allow waste material to enter into an interior chamber 48 of the pouch, and an element to secure the bag in place with the opening 46 connected near the fistula 14. In the present case, then, the bag may be secured to the second end 28 of the wound separator 22, in order to be operatively connected thereto near the fistula 14. In standard ostomy bags, this securement can be obtained by means of a tape that is heat-bonded to the ostomy bag 44 around the opening 46. The tape may have an opening that is positioned in register with the opening 46 of the bag. The side of the tape that faces outwardly from the ostomy bag may be coated with an adhesive, which allows adhesion of the ostomy appliance 44 to the wound separator 22. In one particular embodiment, the ostomy bag 44 includes a cardboard disc defining an orifice that is placed in register with the opening 46 of the ostomy bag 44. The orifice in the cardboard disc is surrounded by an adhesive tape. This adhesive may seal around the open second end 28 of the wound separator 22, and particularly the second flange 50 thereof.

During use of the wound treatment system, the ostomy bag 44 may need to be emptied or replaced periodically. And thus, the ostomy bag 44 is removable from the remainder of the wound treatment system. To that end, the element to secure the ostomy bag 44 to the wound separator 22 and the ostomy bag 44 itself may be constructed as two separable parts, which are connected and disconnected by the user, as desired. This is achieved, for instance, by applying an adhesive tape or spray (as described above, for example) that can release the ostomy bag 44, but retains sufficient tackiness to again form a seal once the ostomy bag 44 is reapplied. Alternatively, a more mechanical element may be used, such as by applying to the wound separator 22, by means of a suitable adhesive, a tape that bears on its outer surface a semirigid plastic snap ring, bonded by conventional means to the tape, that surrounds the opening 46. The ostomy bags 44 then bears a second complementary snap ring mating with the tape one. The complementary snap ring is bonded to the ostomy bag 44 and surrounds the opening 46 therein. The user can therefore apply and remove the ostomy bag 44 from the wound separator 22 without peeling off from the wound separator 22, the element for securing the bag to the wound separator 22. When assembled, the snap ring may provide a tight, leak-free seal.

As described above, the ostomy bag 44 includes an odor-barrier thermoplastic pouch, having an opening 46 in the pouch that is in register with the wound separator 22 in order to receive the stool 16 or other enteric substance. The ostomy bag 44, which, in the illustrated embodiment, has a surface larger than that of the tape for attachment, lies on the wound separator 22 and moves with the wound separator 22 as the skin of the patient body 10 moves. An example of an ostomy bag 44, suitable for the wound treatment system, is the Drainable FirstChoice Pouch, commercially available from Hollister, Inc. of Libertyville, Ill.

Yet another aspect of the present invention provides a wound treatment system including a wound separator 22, as described above, and a device 54 including absorbent dressing materials and/or a vacuum source. An example of such a device is a VAC® device, such as is commercially available from Kinetic Concepts, Inc. of San Antonio, Tex. These two components may be used together and/or may be used in conjunction with an ostomy appliance 44, as described above. This aspect of the present invention, in the illustrated embodiment, includes a sponge 18 having a patient-confronting surface 56, which is positioned facing the wound bed 12. The sponge 18 may be an open-cell structure, including a plurality of passages communicating with the surface of the wound bed 12. Alternatively, the sponge 18 may be a closed-cell structure (i.e., a structure not exhibiting any cells). A drape 58 is placed over the sponge 18 in contact with a top surface 60 thereof. A vacuum source 62 and a vacuum tube 64, with a proximal end 66 connected to the sponge 18 and a distal end 68 connected to the vacuum source 62, may be used to distribute a vacuum through the sponge 18 (in the case of an open-cell structure) or around the sponge (in the case of a closed-cell structure). The wound separator 22 having a sidewall 24 defining an interior chamber 30 is positioned in surrounding relationship to a fistula 14, with at least a portion of an exterior of the wound separator 22 confronting the sponge 18. And thus, the device 54 can be the second component of the wound treatment system referred to above.

This aspect of the present invention thus combines the use of a device 54, such as a VAC® device, in wound healing and the concept of diverting stool 16 or other enteric substances away from the wound bed. Thus, in another aspect, the device 54 heals the wound while stool 16 is diverted from the site into a traditional ostomy bag 44, rather than pooling up and wicking via the sponge 18 across the wound bed 12. In this way, the wound bed 12 remains clean. More particularly, stool 16 is prevented from entering the wound bed 12 by using a size-matched wound separator 22 and a sealant 40, as described above, thereby allowing the sponge 18 to promote wound healing. The sealant 40, as described above, aids in retaining the wound separator 22 in place over the fistula. This leaves the wound bed 12 free to only be contacted by the sponge 18, which assists in healing the wound. The wound separator 22 thus also prevents any stool 16 passing through the fistula 14 from communicating with the sponge 18, as well.

The sponge 18 may also include an orifice 70 defined thereby, with that orifice 70 being sized and positioned such that it overlies the fistula 14 when the sponge 18 is positioned on, or in proximity to, the wound bed 12 of a patient. The sponge 18 includes a bottom or patient-confronting surface 56, a top surface 60, a perimeter 72, and an interior portion 74. As will be apparent to those skilled in the art, the orifice 70 may be cut out of the sponge 18 by a medical technician or other personnel prior to use of the sponge 18, such that the size and location of the orifice 70 can be determined by the medical personnel or other individual(s). The orifice 70 may be cut directly through the sponge 18, such that a continuous orifice 70 is defined by the sponge 18. Or, as shown in FIG. 4, the sponge 18 may be cut into a piece or pieces which are positioned around the fistula 14 in order to effectively define an orifice 70 in the sponge 18 sized and positioned around the fistula 14.

In order that the sponge 18 may be manipulated to include the orifice 70 defined above, the sponge 18 includes material that is amenable to being so manipulated. Thus, the sponge 18, in certain embodiments, includes an open-cell foam material. In a particular embodiment, the sponge 18 may include a hydrophobic polyurethane ether. It will, however, be recognized by those skilled in the art that any biocompatible material may be used that satisfies the purpose of the sponge. Thus, the sponge may alternatively be of a closed-cell material. This material also allows the sponge 18 to be flexible to be placed on, or in proximity to, a wound bed 12, and to be flexible during movement of the patient body 10. It may also absorb fluid in the wound bed 12. And, it can be coated with medication to further promote healing of the wound bed 12. In such an embodiment, the patient-confronting surface 56 of the sponge 18 directly contacts the surface of the wound bed 12. Alternatively, the wound bed 12 (with the exception of the fistula 14) may be covered with soft material, such as foamed plastic or surgical towels (not shown). This covering allows a pressure equalizing substrate to contact the wound bed 12, thereby promoting favorable conditions for the wound bed 12 to heal or for granulation tissue to form. In such an embodiment, the patient-confronting surface 56 of the sponge 18 does not directly contact the wound bed 12. Further, in this embodiment, a layer of separating material (e.g., Vaseline® gauze—not shown) can be applied between the covering and the wound bed 12 to prevent adherence of the covering to the wound bed 12.

In use, the sponge 18 is positioned in a wound bed 12 with the orifice 70 of the sponge 18 surrounding the fistula 14. The wound separator 22 is then also positioned within the orifice 70 of the sponge 18. As can be seen in FIGS. 3-4, the sidewall 24 of the wound separator 22 is particularly positioned between the orifice 70 of the sponge 18 and the fistula 14. This separates the fistula 14, and any stool 16, or other substance passing through the fistula 14 from contacting the sponge 18, thereby eliminating the problem of wicking of stool 16 by the sponge 18 as described in the Background.

The apparatus also includes a drape 58 that is placed over the sponge 18. The drape 58 is placed over the sponge 18 and generally extends beyond its perimeter 72. The drape 58 can have one or more openings formed therein, such as inlet and outlet openings (not shown) for respectively admitting fluid to and extracting fluid from the sponge 18. Or, the drape 58 can include an opening 76 for connection to a vacuum source 62.

The drape 58 can comprise any suitable material, although a semi-permeable membrane may be used for facilitating wound healing by selectively admitting air while retaining liquids and minimizing the risk of infection by excluding contaminates. An example of such a material is Tegaderm®, which is commercially available from the Minnesota Mining and Manufacturing Company (3M) of St. Paul, Minn. Other semipermeable materials are available and can be employed. The drape 58 may include a contact adhesive on one side thereof to facilitate adhering the drape 58 to the patient around a wound site, to the sponge 18, and/or to other components of the wound treatment system. However, a nonadhesive material can be used and retained in place by vacuum pressure (i.e., negative, subatmospheric pressure) within the closed system in combination with positive atmospheric pressure acting externally on the drape 58.

Thus, in certain embodiments, the drape 58 includes an inner, adhesive contact layer 78. The adhesive layer 78 may be disposed on the inside surface of the drape 58, such that it will face the wound bed 12. Such an adhesive layer may include an adhesive flood coated on the inner surface of the drape 58, or alternatively, may include a patterned adhesive on the inner surface of the drape 58 (whether in a random or nonrandom pattern). This adhesive layer 78 can serve to hold the drape 58 to the patient by contacting the patient. Alternatively or additionally, the sponge 18 can be positioned on, or in proximity to, the wound bed 12 such that the adhesive layer 78 of the drape 58 contacts the top surface 60 of the sponge 18. This holds the drape 58 in place over the sponge 18 of the device 54. Still alternatively, the adhesive may contact both the sponge 18 and the patient body 10. More specifically, a portion of the adhesive layer 78 on the inner surface of the drape 58 contacts and adheres to the sponge 18, and the adhesive layer 78 on the inner surface of the drape 58 that extends beyond the outer perimeter 72 of the sponge 18 contacts and adheres to a surface of the patient body 10.

The drape 58 may further include an orifice 80 (in addition to opening 76 for a vacuum source 62 discussed above) disposed therethrough and defined thereby, and sized to match the size of the second opening of the wound separator 22 and/or the size of the opening 46 to any ostomy appliance 44. Thus, as the drape 58 is placed over the wound bed 12 and/or sponge 18, the orifice 80 defined by the drape 58 is placed in register with the second end 28 of the wound separator 22. The adhesive then adheres to the sponge 18 and/or patient surface, thereby holding the drape 58 in place with the orifice 80 in register with the second end 28 of the wound separator 22. The adhesive layer 78, as described above, may be coated over the inner surface of the drape 58 such that it adheres to both the wound separator 22 (and/or the sealant thereon) and the sponge 18. Alternatively, the adhesive layer 78 may be applied to only a portion of the inner surface of the drape 58. In particular, the adhesive may be applied to the inner surface of the drape 58 in proximity to the orifice 80 (e.g. in a ring pattern around the circumference of the orifice 80). Thus, the adhesive causes the drape 58 to be held in place with the orifice 80 in register with the second opening of the wound separator 22. Thus, any stool 16 that passes from the fistula 14 and through the interior chamber 30 of the wound separator 22 may also pass through the orifice 80 in the drape 58. From there it may pass to any other component (e.g., the ostomy appliance 44).

In alternate embodiments, the drape 58 may be applied nonadhesively to a patient. In these embodiments, the drape 58 may also include an orifice 80 that is kept in register with the second end 28 of the wound separator 22.

Further, an ostomy appliance 44, for example the ostomy bag 44 described above, may be operatively connected to the drape 58. Thus, as described above, any orifice 46 in the ostomy bag 44 may be sized and shaped to match the size of the second end 28 of the wound separator 22, and thus may also be sized to match any opening 76 in the drape 58. Thus, as the ostomy bag 44 is placed over the drape 58, the orifice 46 defined by the ostomy bag 44 is placed in register with the orifice 80 defined by the drape 58, and thus also in register with the second end 28 of the wound separator 22. A sealant 52, as described above, may then be used to adhere the ostomy appliance 44 in place with the orifice 40 defined thereby so registered with the orifice 80 of the drape 58 and the second end 28 of the wound separator 22. Thus, in this embodiment, the wound treatment system includes a wound separator 22 forming a diverting column over a fistula 14 in a wound bed 12, a device 54 surrounding the wound separator 22 (particularly, a sponge 18 surrounding the wound separator 22 and drape 58 placed over the sponge 18), and an ostomy appliance (e.g., an ostomy bag 44) placed over the wound separator 22 and drape 58 of the device 54. As a result, the wound separator 22 diverts any stool 16 or other enteric substances away from the wound bed 12 and into the ostomy bag 44 while the device 54 promotes healing of the wound bed 12 itself.

In order to promote this healing of the wound bed 12, the device 54 portion of the apparatus includes a subsystem that provides a vacuum force to the sponge. This subsystem may also be used to remove and add fluids to and from the sponge 18. This subsystem particularly may function to extract fluids, including the patient's blood, serum, etc., from the wound treatment system and also to introduce various fluids, such as antibiotics, analgesics and growth factors into the wound treatment system. Components of the subsystem may include a motorized pump, a fluid collection receptacle, and a control system including pressure control, timing and safety features. A vacuum force can be applied either intermittently for a pulsatile effect, or continuously in a constant pressure mode of operation. The control system may include a suitable microprocessor and is connected to the vacuum source 62. The controller controls pressures, flow rates, timing sequences of intermittent vacuum, and includes control features. The controller can comprise, for example, the control features in a standard VAC® device 54, such as is commercially available from Kinetic Concepts, Inc. of San Antonio, Tex.

A vacuum tube 64 includes a proximal end 66 embedded in the sponge 18 and a distal end 68 connected to the vacuum source 62. The vacuum tube 64 proximal end 66 can be provided with multiple orifices to facilitate distribution of the suction force throughout the sponge 18. The proximal end 66, as in the illustrated embodiment, is connected to the sponge 18 via the opening 76 in the drape 58. Thus, the vacuum force is applied through the sponge, such as when the sponge 18 is of an open-cell structure. Alternatively, when the sponge 18 is of a closed-cell structure, the proximal end 66 of the vacuum tube 64 is not embedded in the sponge 18, but rather, is positioned through the opening 76 in the drape 58 and in proximity to the sponge 18 to distribute the vacuum around the sponge 18.

Thus, wound drainage can be accomplished by applying the sponge 18, which can be cut to an appropriate size and configuration for a particular wound, covering it with a drape 58 and forming an outlet opening 76 therein. Negative vacuum pressure is communicated to, through, or around the sponge 18. The controller can be programmed to provide either continuous or intermittent suction via the vacuum source 62 at suitable predetermined intervals and pressures.

The hydrophobic, porous characteristics of the sponge, in the illustrated embodiment, 18 facilitates efficient passage of patient fluids therethrough, including various matter such as serum, protein, blood, etc. Moreover, creating subatmospheric pressure (i.e., negative pressure) within the closed environment of the wound treatment system can help control edema in the wound area and in the surrounding tissues. The edema-countering effects of the wound treatment system can be varied by setting the controller at different appropriate pressure settings and timing sequences.

By way of example, the following steps may be involved in the treatment of a fistula 14:

First, the wound bed 12 and surrounding area is cleaned and debrided as necessary. Any additional therapeutic treatments such as skin grafts or pharmaceutical preparations are then applied to the wound bed 12.

Second, a viscous sealant 40 that is not readily dissolved by the output from the fistula 14 site, such as ostomy paste, is applied around the outside diameter of the fistula 14. The sealing agent is applied in such a manner as to mate with the wound separator 22 and provide an airtight seal (alternatively, as described above, this seal could be integrated into the wound separator 22).

Third, an appropriately sized and shaped wound separator 22 is selected and applied so that it surrounds the fistula 14 leaving the smallest amount of exposed wound bed 12 possible within the bounds of the wound separator 22. The wound separator 22 and the sealant 40 are to act as a conduit for the fistula 14 output (i.e., stool 16 or other enteric substances), thereby protecting the rest of the wound bed 12 from contamination by the fistula 14 output.

Fourth, the wound bed 12 with the exception of the fistula 14 (fistulas) is covered with soft material such as foamed plastic or surgical towels. The purpose of the wound bed 12 cover is to allow a pressure equalizing substrate to remain in contact with the wound bed 12 in order to allow favorable conditions for the wound bed 12 to heal or granulation tissue to form. A layer of separating material to prevent adherence of the wound bed 12 to the overlying soft substrate such as Vaseline® gauze may also be applied.

Fifth, an airtight bandage material (a drape 58) such as Opsite® (commercially available from Smith & Nephew, of London, England) is applied covering the wound including the fistula 14 and device 54. The airtight bandage (drape 58) extends beyond the border of the wound with enough overlap to allow an airtight seal with sound tissue surrounding the wound once air is removed from around the wound.

Sixth, the area of airtight bandage covering the interior chamber portion of the device 54 is trimmed so as to allow free passage of material produced by the fistula 14 through the conduit of the interior chamber. Extra sealant (e.g., ostomy paste) may be introduced around the base 38 of the fistula 14 at this time in order to allow a more robust seal and to provide extra protection to the area immediately surrounding the fistula 14 from contamination by the fistula output.

Seventh, the entire area covered by the airtight bandage is checked for potential areas of air leakage paying close attention to the periphery and interface with the device 54. Areas of potential leakage are patched with airtight bandage as needed.

Eighth, a self-adhesive ostomy appliance 44 is applied over the device 54 so as to allow passage of the fistula 14 output to travel through the device 54 into the ostomy appliance 44.

Ninth, a small slit or hole is made in the airtight bandage (drape 58) and a vacuum source 62 is attached to this hole in the drape 58 in order to provide an area of low pressure to exist within the bounds of the drape 58. The purpose of this is to allow the ambient pressure to firmly appose the device 54, the sealant substance, the drape, and the ostomy appliance 44 in an airtight and fluid tight manner.

Tenth, once vacuum is applied, the assembly is rechecked for leakage and repaired as needed.

The ostomy appliance 44 can be changed as a unit without violating the integrity of the airtight seal. This may be required when the ostomy appliance 44 is full or the area bounded by the device 54 requires therapeutic intervention.

Finally, the assembly can be removed if a leak develops, therapeutic access is required to the tissues protected by the drape, or when the device 54 is no longer deemed necessary.

As various changes could be made in the above-described aspects and exemplary embodiments without departing from the scope of the invention, it is intended that all matter contained in the above description shall be interpreted as illustrative and not in a limiting sense.

What is claimed is:

1. A wound treatment system comprising:
   a sponge including a first surface adapted to confront a wound bed of a patient;
   a drape in contact with a second surface of the sponge, the second surface being substantially opposite said first surface;
   a vacuum source for distributing a vacuum force through said sponge;
   a vacuum tube having a proximal end connected to the sponge and a distal end connected to said vacuum source; and a wound separator having a sidewall defining an interior chamber, wherein at least a portion of an exterior of said sidewall confronts at least an interior portion of said sponge, the wound separator adapted to confront an opening in the wound bed, such that the opening in the wound bed is in communication with the interior chamber of the wound separator and the opening in the wound bed is not substantially in communication with the sponge or with the wound bed exterior to the wound separator, wherein the interior chamber of the wound separator is open at a first end thereof, the first end adapted to be placed in direct contact with the wound bed and in a surrounding relationship to a fistula.

2. The wound treatment system of claim 1, wherein the sponge further defines an orifice therethrough, and the wound separator is positioned in the orifice.

3. The wound treatment system of claim 2, wherein said first end includes a first flange extending outwardly therefrom relative to a longitudinal axis of the wound separator.

4. The wound treatment system of claim 3, wherein the second end is open, and further comprising a second flange operatively coupled to and extending radially outwardly from the second end of the wound separator.

5. The wound treatment system of claim 1, further comprising an adhesive on a surface of the drape in contact with said second surface of said sponge.

6. The wound treatment system of claim 1, wherein said drape is applied non-adhesively to a patient.

7. The wound treatment system of claim 6, wherein said drape is retained on said patient by the vacuum force.

8. The wound treatment system of claim 1, wherein said drape defines an orifice in fluid communication with the interior chamber of the wound separator.

9. The wound treatment system of claim 1, further comprising an ostomy appliance operatively connected to the drape.

10. The wound treatment system of claim 9, wherein said ostomy appliance further comprises a bag of thermoplastic material having an outer surface and defining an interior chamber.

11. The wound treatment system of claim 10, wherein said bag further defines an opening, said opening being in fluid communication with the interior chamber of the wound separator and the interior chamber of the bag.

* * * * *

UNITED STATES PATENT AND TRADEMARK OFFICE
CERTIFICATE OF CORRECTION

| | |
|---|---|
| PATENT NO. | : 8,771,243 B2 |
| APPLICATION NO. | : 12/023251 |
| DATED | : July 8, 2014 |
| INVENTOR(S) | : Joseph Khan et al. |

It is certified that error appears in the above-identified patent and that said Letters Patent is hereby corrected as shown below:

In the Specification

Column 5,
Line 49 reads "exits" and should read --exists--.

Column 6,
Line 55 reads "exits" and should read --exists--.

Column 7,
Line 47 reads "bags" and should read --bag--.

Column 11,
Lines 39-40 read "characteristics of the sponge, in the illustrated embodiment, 18 facilitates" and should read --characteristics of the sponge 18, in the illustrated embodiment, facilitate--.

Signed and Sealed this
Seventh Day of October, 2014

Michelle K. Lee
*Deputy Director of the United States Patent and Trademark Office*